(12) United States Patent
Göbel

(10) Patent No.: US 6,551,272 B2
(45) Date of Patent: *Apr. 22, 2003

(54) STOMACH PROBE

(76) Inventor: Fred G. Göbel, Blumenstrasse 30, D-69115 Heidelberg (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/254,429

(22) PCT Filed: Sep. 10, 1997

(86) PCT No.: PCT/EP97/04960

§ 371 (c)(1),
(2), (4) Date: Aug. 10, 1999

(87) PCT Pub. No.: WO98/13090

PCT Pub. Date: Apr. 2, 1998

(65) Prior Publication Data

US 2001/0041861 A1 Nov. 15, 2001

(30) Foreign Application Priority Data

| Sep. 10, 1996 | (DE) | ............................................ 196 36 654 |
| Sep. 23, 1996 | (DE) | ............................................ 196 54 910 |
| Sep. 23, 1996 | (DE) | ............................................ 196 38 935 |
| Jun. 7, 1997 | (DE) | ............................................ 197 24 096 |

(51) Int. Cl.$^7$ ............................................. A61M 37/00
(52) U.S. Cl. ................................................. 604/96.01
(58) Field of Search ......................... 604/96.01, 100.01, 604/264, 99.01, 102.01, 102.02, 910; 128/207.14, 207.15

(56) References Cited

U.S. PATENT DOCUMENTS 3,640,282 A    2/1972   Kamen et al.

(List continued on next page.)

FOREIGN PATENT DOCUMENTS

| DE | 24 00 569 | 7/1975 |
| DE | 24 12 553 | 9/1975 |
| DE | 30 18 608 | 1/1981 |

(List continued on next page.)

*Primary Examiner*—Anhtuan T. Nguyen
*Assistant Examiner*—Ann Y Lam
(74) *Attorney, Agent, or Firm*—Burns, Doane, Swecker & Mathis, L.L.P.

(57) ABSTRACT

The invention is based on the intention of creating a stomach probe with which a watertight closure of the oesophagus is possible. The stomach probe, according to the invention, is characterized by a tampon-bladder for watertight closure of the oesophagus, in which the tampon-bladder forms from flexible and/or elastic material at least a closed inner cavity for the reception of a fluid medium, through a means (11) of establishing a prescribed pressure for the medium in the tampon-bladder (16) by an inner lumen forming the actual stomach probe, from which an outer hose-like lumen (18) extending to the tampon-bladder (16) is so arranged that between the outer lumen (18) and the inner lumen (17) a channel is formed connected to the inner cavity of the tampon-bladder (16) arranged on the outer lumen (18) by a number of openings (20), whereby the inner cavity of the tampon-bladder (16) is connected via the canal formed between the inner and outer lumina (17, 18) with the means of production of pressure in the tampon-bladder, that is, with a suitably graded reservoir or equalizing vessel (11) for the liquid medium situated above the tampon-bladder and outside the patient.

14 Claims, 4 Drawing Sheets

U.S. PATENT DOCUMENTS

Figure 1:
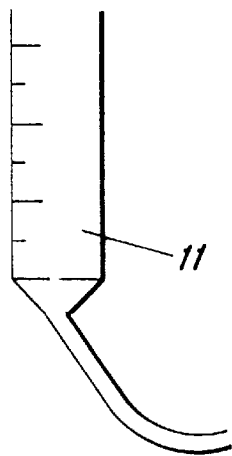
Figure 1:
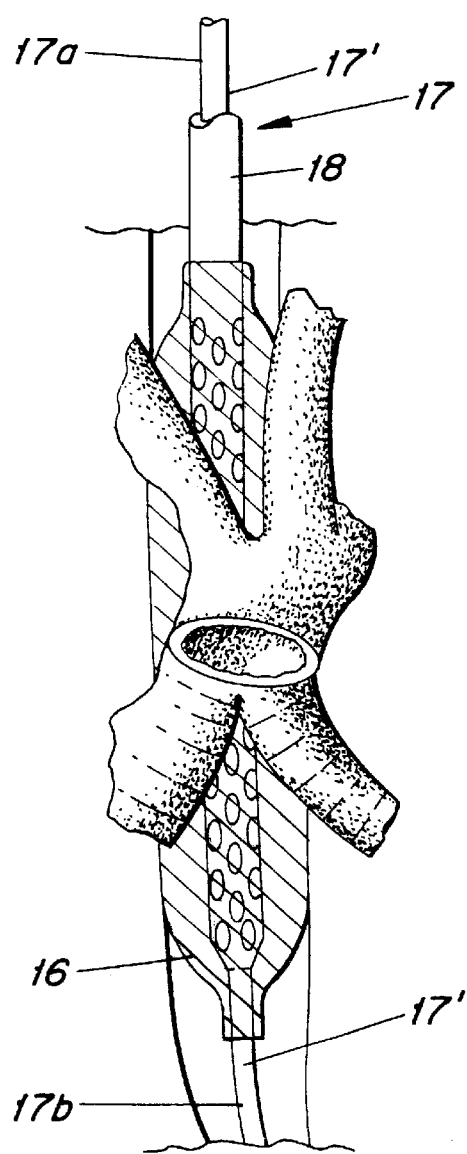

| | | | |
|---|---|---|---|
| 3,669,098 A | | 6/1972 | Takahashi |
| 3,766,924 A | | 10/1973 | Pidgeon |
| 3,848,605 A | | 11/1974 | Harautuneian et al. |
| 3,901,246 A | | 8/1975 | Wallace |
| 3,913,565 A | * | 10/1975 | Kawahara ................... 128/2 |
| 3,931,822 A | | 1/1976 | Marici |
| 4,020,849 A | | 5/1977 | Jackson |
| 4,022,217 A | | 5/1977 | Rowean |
| 4,090,518 A | | 5/1978 | Elam |
| 4,091,816 A | | 5/1978 | Elam |
| 4,156,428 A | | 5/1979 | Henkin |
| 4,182,344 A | * | 1/1980 | Benson ................. 128/207.15 |
| 4,230,108 A | | 10/1980 | Young |
| 4,235,239 A | | 11/1980 | Elam |
| 4,387,711 A | | 6/1983 | Merry |
| 4,445,892 A | | 5/1984 | Hussein et al. |
| 4,449,523 A | | 5/1984 | Szachowicz et al. |
| 4,526,196 A | * | 7/1985 | Pistillo ...................... 137/557 |
| 4,543,951 A | * | 10/1985 | Phuc .................... 128/204.25 |
| 4,583,917 A | | 4/1986 | Shah |
| 4,700,700 A | | 10/1987 | Eliachar |
| 4,762,125 A | | 8/1988 | Leiman et al. |
| 4,791,923 A | | 12/1988 | Shapiro |
| 4,917,107 A | | 4/1990 | Bell et al. |
| 5,033,466 A | * | 7/1991 | Weymuller, Jr. ....... 128/207.15 |
| 5,038,777 A | * | 8/1991 | Dunn .................... 128/207.14 |
| 5,040,531 A | | 8/1991 | Coleman et al. |
| 5,304,134 A | | 4/1994 | Kraus et al. |
| 5,398,692 A | * | 3/1995 | Hickey ....................... 128/673 |
| 5,456,251 A | | 10/1995 | Fiddian-Green |
| 5,462,528 A | | 10/1995 | Roewer |
| 5,490,839 A | | 2/1996 | Wang et al. |
| 5,638,813 A | | 6/1997 | Augustine |
| 5,976,107 A | * | 11/1999 | Mertens et al. ............... 604/96 |

FOREIGN PATENT DOCUMENTS

| | | |
|---|---|---|
| DE | 30 36 192 | 5/1982 |
| DE | 32 09 413 | 9/1983 |
| DE | 34 35 849 | 4/1986 |
| DE | 35 42 260 | 6/1986 |
| DE | 87 11 592.1 | 10/1987 |
| DE | 39 18 956 | 12/1989 |
| DE | 40 12 296 | 10/1991 |
| DE | 41 32 687 | 4/1993 |
| DE | 23 41 833 | 2/1995 |
| DE | 295 11 468 | 11/1995 |
| DE | 195 47 538 | 6/1997 |
| DE | 196 38 935 | 3/1998 |
| DE | 196 54 910 | 3/1998 |
| EP | 0 277 797 | 8/1988 |
| EP | 0 596 517 | 5/1994 |
| EP | 0 697 205 | 2/1996 |
| FR | 2 380 786 | 2/1978 |
| JP | 3-198864 | 8/1991 |
| JP | 5-84341 | 11/1993 |
| WO | WO 93/23107 | 11/1993 |

* cited by examiner

STOMACH PROBE

This application is a national stage filing under 35 U.S.C. §371 of International Application No. PCT/EP97104960 filed on Sep. 10, 1997, which International Application was not published by the International Bureau in English.

Material rising up into the pharynx from the stomach and intestinal tract represents, particularly for the unconscious patient being ventilated, a permanent reservoir of microbes, and may provoke or exacerbate pulmonary infection from the lower pharynx on intubation. Artificially ventilated intensive care patients are looked after through secretion-stimulating gastric probes or feeding tubes whose throughput as a rule is still insufficient to put a stop to gastro-oesophogeo-pharyngeal reflux beside or along them. As a result the greater number of sedated or artificially ventilated patients are virtually overwhelmed by high-grade bacterially contaminated material in the pharyngeal, nasal and postnasal regions.

On account of various difficulties in the search for a simple mechanical oesophageal or gastric blockade tolerable in the long term this infective problem potential could not until now be satisfactorily resolved. What was tried out therapeutically, and generally tolerated, was essentially medicinal/antibiotic (e.g. selective bowel decontamination).

Since the structures of the oesophageal wall react extremely sensitively to persistent pressure or tension, the conventional blocking techniques, in which the walls of the attached structures are placed under tension (as a rule by a balloon) are not, or only with limitations, applicable in the case of the oesophagus.

The purpose of the invention is to rectify the disadvantages just mentioned and to present a stomach probe with which closing off or filling out of the oesophagus is possible without deleterious effect on its wall structures.

For the resolution of this aim the stomach probe is equipped with the characteristics of Patent claim 1.

The oesophagus is a dynamic structure constantly changing in shape. The tonus of its wall, and its lumen, are subject to considerable active and passive functional fluctuations. Tamponization of the oesophagus by a bladder like that of the invention fits in with their physiological dynamic and thus guarantees a simple self-regulating and well-tolerated closure or filling of the gullet. Regurgitation of material highly contaminated with microbes from the stomach and gut regions into the oral, nasal or pharyngeal cavities is prevented by the invention. By means of the invention gastro-oesophageal-pharyngeal reflux is prevented by a simple self-regulating and well-tolerated mechanical blockade in the oesophageal region. Drainage of stomach contents is thus guaranteed to take place through an ordinary stomach or feeding probe.

Ulcerations or necroses of the oesophageal wall structures as a result of long-term blocking are excluded by the most far-reaching pressure-passive actions of the tampon-bladder described in the invention.

Immediately adjoining structures such as the great vessels, the accompanying nerves, the trachea and main bronchi, the lungs themselves and, not least, the heart, particularly the left atrium, are, in contrast to conventional blocking, not endangered.

The inner cavity of the tampon-bladder may be filled with the medium, through a channel lying between the inner and outer lumina, from a filling device connected to the channel. Simply operated examples of such a filling device are a reservoir or equalizing vessel, particularly one situated outside the patient. A supply of the medium sufficient to fill the inner cavity of the tampon-bladder, and in addition to allow for the abovementioned functional fluctuations of the lumen and the tonus of the oesophageal wall through further outflow or intake of the medium by expansion and collapse of the tampon-bladder, is kept in the reservoir or equalizing vessel.

In this connection it could be seen as an additional advantage for the medium to be actively led into the inner cavity of the tampon-bladder or withdrawn from the inner cavity through the channel. Such active supply and withdrawal take place through a pump which is regulated preferably to compensate for any extensive pressure-passive fluctuations in the tampon-bladder.

So that a medium is used which can be supplied or withdrawn rapidly and at the same time has a thermal capacity high enough for the adjustment of the temperature measured inside the oesophagus, it can be a fluid such as for example water or equivalent. Such a medium is simple and quick to pump and easily adjustable in temperature.

Another medium which is distinguished by compressibility as well as a certain adaptability of its own to the fluctuations mentioned above is, for instance, a gaseous one. Filling apparatus, reservoir, equalizing vessel and pump may all be used with any suitable medium and are designed accordingly.

Further advantageous embodiments of the invention derive from features in the Claims below.

Figure 3:
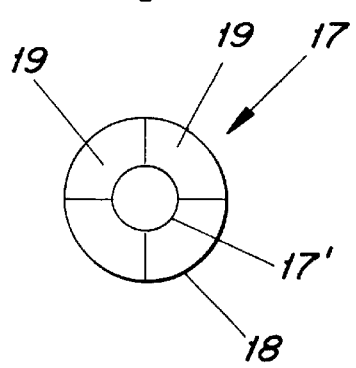
Figure 2:
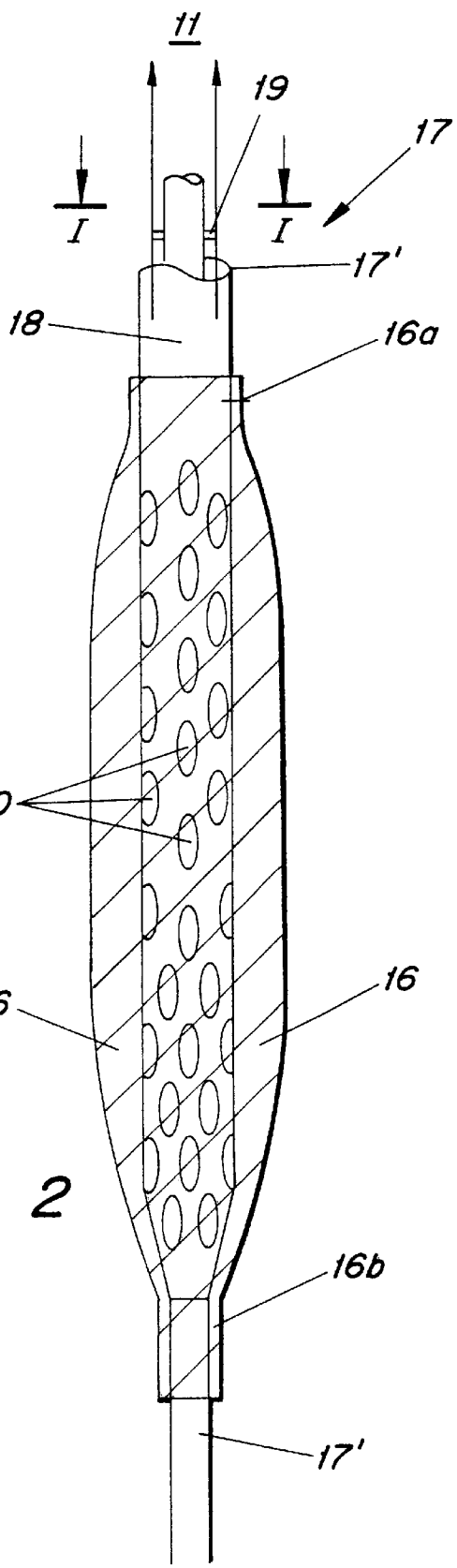
Figure 4:
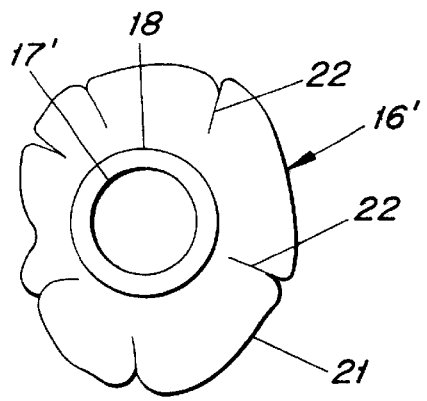
Figure 5:
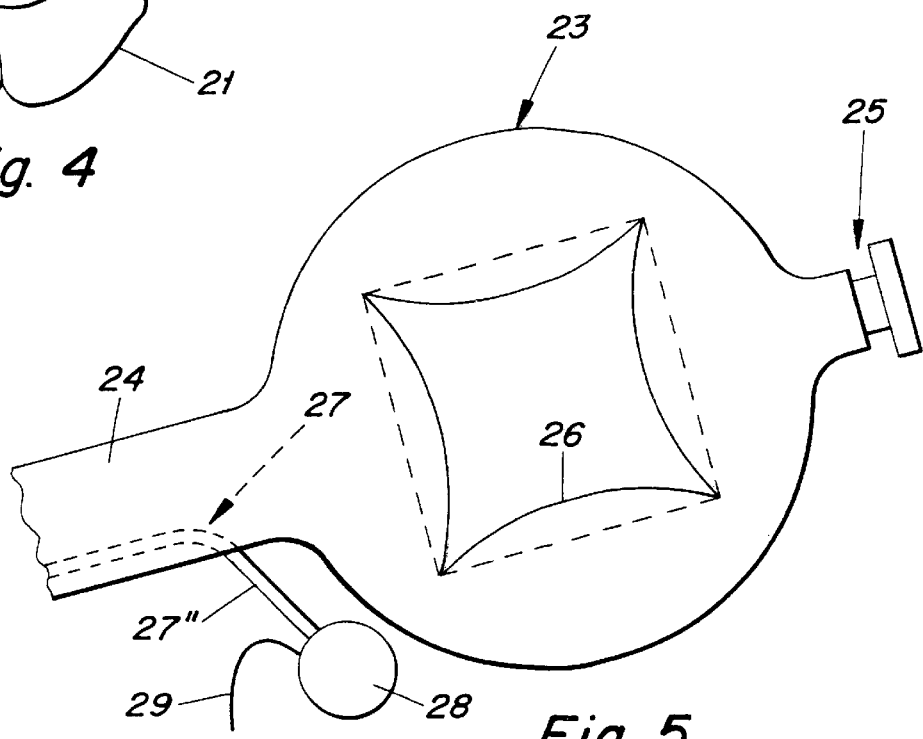
Figure 7:
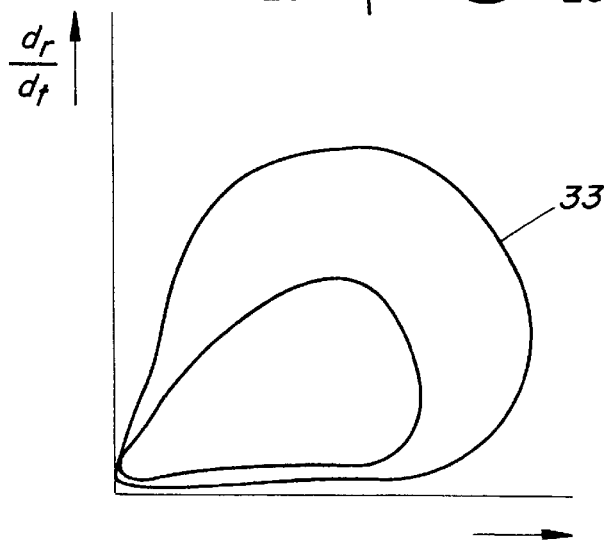
Figure 6:
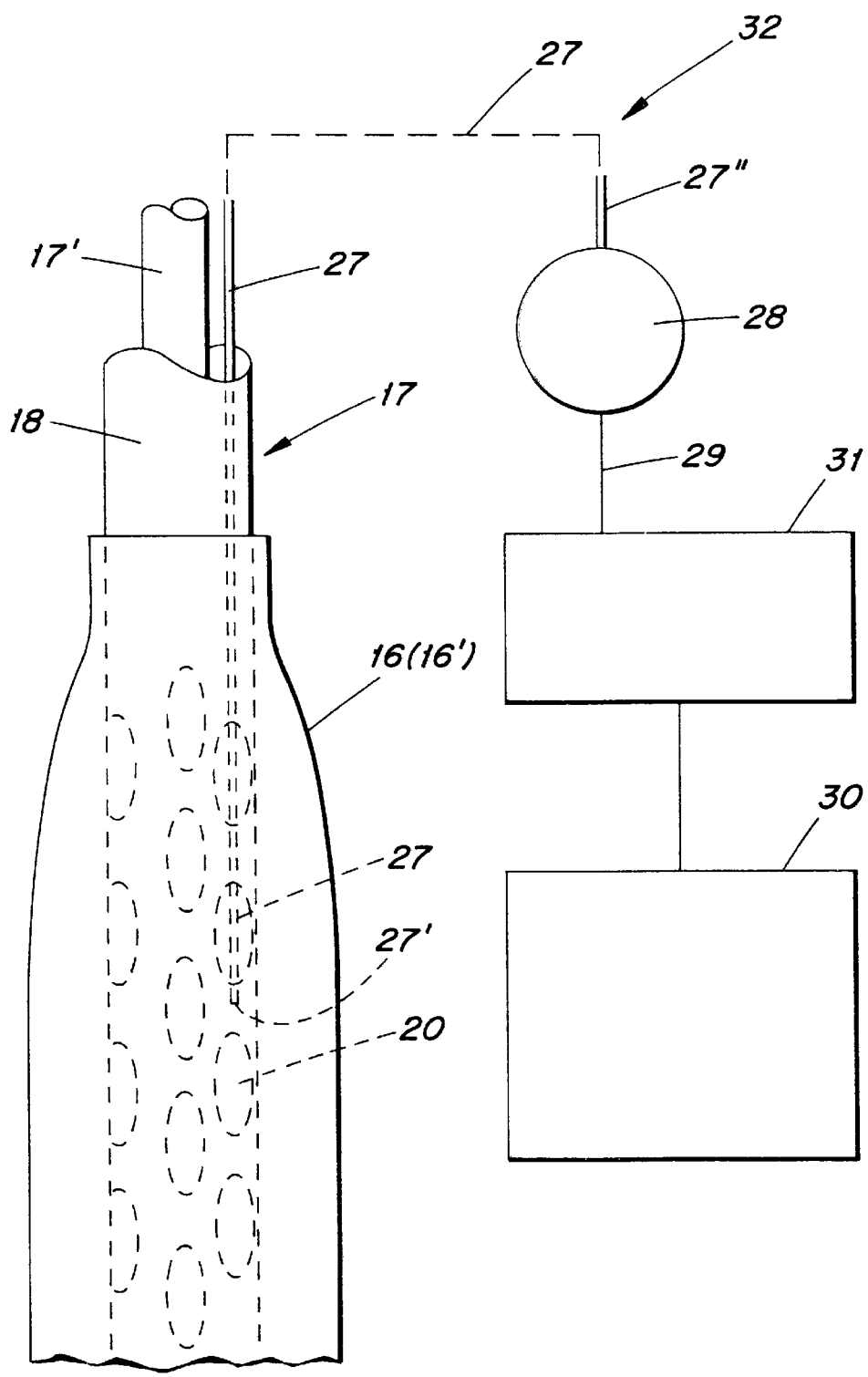

The invention is more precisely explained with the help of the following Figures as operational examples:

FIG. 1 a frontal view of the oesophagus (gullet) with adjoining anatomical structures. Also shown is the combination of stomach probe and tampon-bladder shown subsequently;

FIG. 2 the construction of the device, with stomach probe, tampon-balloon, wide-bore connection and extracorporeal reservoir in a recommended operational form of the invention;

FIG. 3 a section of the line 1—1 of FIG. 2;

FIG. 4 a simplified representation of a section through the wall of a further possible operational form for the tampon-bladder of the stomach probe;

FIG. 5 a ball-shaped pressure-container manufactured from an elastic material, e.g. rubber, for use with the stomach probe of FIGS. 1–3 in place of the open reservoir;

FIG. 6 a simplified representation of a stomach probe with a pressure-measuring system;

FIG. 7 a simplified representation of a signal from the pressure-sensor led off and shown as a diagram on a screen;

In FIG. 1 is shown the topographical relation to the relevant adjoining anatomical structures (trachea and main bronchi and great arterial vessels) of the correctly-placed apparatus or stomach probe 17, consisting of a hose-like probe element or lumen 17' with tampon-bladder 16. As indicated, a tampon-bladder 16 about 15 to 20 cm long and filled with water or another suitable medium is positioned in the vicinity of the middle third of the oesophagus. Through the tampon-bladder 16 run the regular feeding-tube or stomach probe and the lumen 17', that come to lie with the lower end 17b in the stomach, and the upper end 17a controlled orally or nasally. This way enteral feeding and the drainage of stomach and gut secretion are guaranteed.

The tampon-balloon 16, filled with water or another suitable medium, communicates via a second, concentric, outer lumen of the greatest possible diameter with an extracorporeal reservoir 11. In FIG. 1 this tampon-balloon is indicated by cross-hatching.

In FIG. 2 the principle of the entire apparatus, consisting of the probe or probe-hose 17' and tampon-bladder 16, is shown in more detail. The stomach-probe 17 is surrounded in the region of the tampon-bladder 16, as well as in the sector of the apparatus extending from the tampon-bladder to the extracorporeally placed reservoir 11, by a concentrically arranged outer lumen 18. This lumen, for choice as large as possible, permits a rapid to-and-fro exchange of fluid between the tampon-bladder 16 and reservoir 11. On the principle of communicating pipes the outer lumen 18 is responsible for a continuous shape-maintaining self-regulating filling of the tampon-balloon 16, without thereby putting the wall of the oesophagus under any notable degree of stress. The tamponade of the gullet can thus be maintained with a minimal continually sustained pressure to keep up the filling. At the same time the outer lumen 18 is shored up by bridge-like structures or dividing fixtures 19 between the outer and inner walls of the probe.

In the region 16a to 16b enclosed by the tampon-balloon 16, the wall of the outer lumen 18 of the concentric probe, which has two lumina, is perforated 20 like a sieve. When in the act of swallowing or vomiting a wave of contraction of the oesophagus directed towards either the stomach or the pharynx ensues, the perforations in the outer wall of the probe permit a shift of volume from the tampon-bladder 16 into the outer lumen 18 of the probe, and consequently a rapid exchange of volume between contracted and ready but relaxed sectors of the probe. The sieve-like construction of the outer lumen of the probe thus makes rapid redistribution of balloon-filling inside the tampon-bladder readily possible and so puts up a slight to overwhelming resistance against a contraction wave being transmitted by the act of swallowing at a speed of about 2–3 cm/second. Greater shifts of volume, which cannot be evened out immediately inside the tampon-bladder, are possibly transmitted away to the extracorporeal reservoir 11. The reservoir 11 is situated outside and above the patient and takes the form of a graduated water-column. The probe 17 and its constituents 17', 16 and 18 are constructed of a body-tolerated sufficiently elastic material, like that already used for ordinary feeding-probes.

The tampon-bladder 16 is constructed from an equally body-tolerated foil-like elastic material, which follows the changes of the oesophagus in form and volume without wrinkling, and clings to its epithelium. It is preferably a body-tolerated soft foil with properties resembling those of latex skin. The connection between the tampon-bladder 16 and the lumen 17' at 16a and 16b is brought about by adhesion, welding and adhesion, bandaging or something similar.

To ensure correct placing of the apparatus and its tampon-bladder in the oesophagus, the apparatus is distinguished by a coloured marker corresponding to its later position at the corner of the mouth with oral, or at the nostril with nasal, insertion.

With use of the reservoir 11 the water-pressure in the tampon-bladder 16 is decided solely by the column of water reaching to the reservoir 11, so that the reservoir 11 has a level slightly above the tampon-bladder 16. In this way a very constant inner pressure, lying marginally above the atmospheric, is maintained in the tampon-bladder 16.

FIG. 4 shows in very simplified representation a section through the tampon-bladder 16a in a further possible operational form of the invention. The wall 21 of this tampon-bladder is made of a very thin flexible material (foil) and on the inside of the tampon-bladder 16a forms many persistent folds 22. To these folds 22 the material forming the wall 21 for instance is suitably adherent or otherwise affixed, so that on expansion of the inner cavity of the tampon-bladder 16a by slight pressure the folds open out and consequently can press the tampon-bladder 16a with its wall 22 closely to the wall of the oesophagus, and in fact to a variety of anatomical situations.

It can be assumed that in the system described in the context of FIGS. 1–3 the pressure inside the tampon-bladder 16, lying slightly above atmospheric pressure, is set by the fluid- or water-column with the help of the open, extracorporeal reservoir 11.

FIG. 6 shows a closed reservoir 23, ball-shaped and made out of an elastic material such as rubber. The inner cavity of the reservoir 23 is connected via the large-diameter connecting hose 24 with the outer lumen 18 of the otherwise not further represented stomach probe. In addition the reservoir 23 has a plug-like stopper 25, through which filling with water can be done, in fact in such a way that the whole system, namely the tampon-bladder 16 or 16', the lumen 18, the connecting hose 24 and the reservoir 23 are completely filled with water. Filling follows up to a limited pressure, in fact the kind that comes from the elastic properties of the wall of reservoir 23, and the requisite limited pressure ensues. To reach the desired pressure an optical marker 26 is placed on the outer surface of the reservoir wall 23, in fact delineated in such a way that on account of the elastic stretching of the wall of the reservoir 23 at the correct pressure this symbol 26 takes on an easily perceptible symmetrical shape. In the operational form shown the symbol 26 is a quadrilateral of which the corner points form the corner points of a square whose sides appear concave on the outside of unpressurized reservoir 23, so that on increasing pressure in the reservoir this marker 26 assumes the form of a square.

Other shapes are also conceivable for the symbol 26, for instance an oval closed line which with the correct inner pressure of the reservoir 23 changes to a circular shape, etc.

Consequently with the help of the symbol 26 the inner pressure of the tampon-bladder 16 or 16' can of course also be brought to a pressure lying slightly above atmospheric pressure. The closed system with the reservoir 23 has the advantage that this reservoir can be placed for instance on a divan or bed beside the head of the patient.

FIG. 6 shows the stomach probe of FIG. 2 once again in simplified form. A small thin measuring tube is shown as 27, which at its one, open, end 27' is located in the region of lumen 18 surrounded by the tampon-bladder 16, in fact in the vicinity of the openings or apertures 20. The other end of the measuring tube 27 leads off the outer lumen 18 and hence off the connecting hose 24, and is shown in FIG. 5 as 27". At this 27" end is located a pressure gauge 28 which converts the pressure inside the measuring tube into an electrical signal proportionate to the pressure. The pressure gauge 28 is connected through a measuring-lead to among others an electronic device 31 showing a screen 30, which may for example be that of a calculator or PC. The interior of the measuring-tube 27 is completely filled with the fluid (water), so that the pressure exerted in the outer lumen in the region of the tampon-bladder 16 or 16' appears immediately, that is to say as far as possible without delay, on the pressure-gauge 28. With this measuring apparatus intrathoracic pressures or changes in pressure can be measured without problems, particularly the mobility of the oesophagus, the respiration and also the atrial and ventricular actions of the heart. In particular the depth of anaesthesia can also be determined in a patient under anaesthesia. The measuring-tube 27 and the pressure-gauge form the measuring-probe 32.

The pressure determined with the measuring-probe 32 can be assessed in various ways and/or be shown on the screen. For example an indication can be given in the diagram reproduced in FIG. 7, in which the pressure is depicted on the abscissa and the first succession of temporal pressure changes on the ordinate. By this means a persistent cluster of curves from the curves 33 enclosed in it is produced in the visible region of the screen, by which the time component of this cluster of curves is taken into consideration by means of distinguishing colouration, that is, by alternation of colours at settled time intervals.

Key to Illustrations

11 Reservoir
16, 16' Tampon-bladder
16a, 16b End of tampon-bladder
17 Stomach probe
17', 18 Lumen
19 Divider
20 Opening
21 Wall
22 Fold
23 Reservoir
24 Connecting hose
25 Stopper
26 Marker
27 Measuring tube
27', 27" End
28 Sensor or Pressure-gauge
29 Measuring lead
30 Screen
31 Electronic measuring device
32 Measuring probe
33 Curve (of graph)

What is claimed is:

1. A stomach probe for sealing an oesophagus of a patient so that physiological shaping and function of the oesophagus is not compromised, comprising:

a tampon-bladder placeable in the oesophagus and forming an inside space for the reception of a medium, said tampon-bladder formed from a flexible and/or elastic material;

a first lumen extending through said tampon-bladder;

a second lumen reaching into the tampon-bladder, said second lumen including a channel for communicating with an inner cavity of the tampon-bladder, wherein the inner cavity of the tampon-bladder is fillable through said channel by means of a filling device connectable to the channel, said filling device ensuring a slight, shape-maintaining filling pressure inside said tampon-bladder;

a wall of said second lumen being provided with a plurality of openings connecting an interior of the tampon-bladder with an interior of the second lumen, said openings being sieve-like, being arranged over the length of said second lumen, and being sufficient in number and size, and the tampon bladder being sufficient in length and diameter for enabling a rapid exchange of volume of the medium between contracted and relaxed sectors of the tampon-bladder upon a wave of contraction of the oesophagus.

2. The stomach probe according to claim 1, wherein the filling device comprises a reservoir or equalizing device for the medium above the tampon-bladder, comprising a fluid column communicating with the interior of the tampon-bladder and adjusting a pressure in the tampon-bladder.

3. The stomach probe according to claim 1, wherein the tampon-bladder is part of a closed fluid system.

4. The stomach probe of claim 2, wherein the equalizing device comprises at least one reservoir with tan inner cavity communicating with the tampon-bladder, said inner cavity being closed by a flexible or elastic wall at least in a sector thereof.

5. The stomach probe according to claim 2, wherein the reservoir or equalizing device forms a means for the adjustment of a prescribed pressure in the tampon-bladder.

6. The stomach probe according to claim 1, wherein the medium is a fluid.

7. The stomach probe according to claim 1, wherein in the medium is gaseous.

8. The stomach probe according to claim 1, wherein the tampon-bladder is about 15–20 cm long.

9. The stomach probe according to claim 1, wherein the tampon-bladder is formed into a plurality of folds.

10. The stomach probe according to claim 9, wherein the wall of the tampon-bladder is fixed or adhered to the fold.

11. The stomach probe according to claim 1, wherein the first lumen is arranged relative to said second lumen in a manner that said channel is formed between said first and second lumen.

12. The stomach probe of claim 1, wherein the second lumen is positioned relative to the first lumen forming the actual probe by means of bridge-like structures or dividing fixtures.

13. The stomach probe of claim 1, wherein a pressure measuring probe includes a measuring end which is located in the tampon-bladder or in a cavity communicating with the inner cavity of the tampon-bladder.

14. The stomach probe according to claim 13, wherein the probe is formed by measuring-tube which forms the measuring end at its open end and a the other end, extracorporeally, incorporates a pressure-sensor or a pressure-transducer, and that he measuring-tube is filled with the fluid in such a way that he whole channel of the measuring-tube between the two ends is filled with fluid.

* * * * *